(12) United States Patent
Liolios et al.

(10) Patent No.: US 11,576,878 B2
(45) Date of Patent: Feb. 14, 2023

(54) ORAL SOLUTIONS COMPRISING LISDEXAMFETAMINE SALTS

(71) Applicant: Labomed Pharmaceutical Company S.A., Attica (GR)

(72) Inventors: Georgios Liolios, Chalandri Attica (GR); Ioannis Psarrakis, Lavrion (GR)

(73) Assignee: LABOMED PHARMACEUTICAL COMPANY S.A., Koropi (GR)

( * ) Notice: Subject to any disclaimer, the term of this patent is extended or adjusted under 35 U.S.C. 154(b) by 136 days.

(21) Appl. No.: 16/961,784

(22) PCT Filed: Apr. 16, 2020

(86) PCT No.: PCT/EP2020/060777
§ 371 (c)(1),
(2) Date: Jul. 13, 2020

(87) PCT Pub. No.: WO2021/136602
PCT Pub. Date: Jul. 8, 2021

(65) Prior Publication Data
US 2021/0401781 A1  Dec. 30, 2021

(30) Foreign Application Priority Data
Dec. 30, 2019  (EP) .................... 19386059

(51) Int. Cl.
*A61K 31/165* (2006.01)
*A61K 9/00* (2006.01)
*A61K 9/08* (2006.01)

(52) U.S. Cl.
CPC .......... *A61K 31/165* (2013.01); *A61K 9/0053* (2013.01); *A61K 9/08* (2013.01)

(58) Field of Classification Search
CPC .................................................. A61K 31/165
See application file for complete search history.

(56) References Cited

U.S. PATENT DOCUMENTS 7,105,486 B2  9/2006  Mickle et al.

FOREIGN PATENT DOCUMENTS

| WO | WO-2006/121552 A2 | 11/2006 | |
| WO | WO-2006121552 A2 * | 11/2006 | ........... A61K 31/165 |

OTHER PUBLICATIONS

Goodman, "Lisdexamfetamine Dimesylate: the First Prodrug Stimulant", Psychiatry, vol. 4, pp. 39-46, (2007) (Year: 2007).*
David, "FASTtrack Pharmaceutics—Dosage Form and Design", London and Chicago: Pharmaceutical Press, pp. 1-24 (2008) (Year: 2008).*
Krishnan; J Clin Pharmacol 2008, 48, 293-302. https://doi.org/10.1177/0091270007310381 (Year: 2008).*
Vyvanse (lisdexamfetamine dimesylate capsule). Package insert. Physicians Total Care, Inc. 2012. (Year: 2012).*
Robert G. Strickley et al "Pediatric drugs—a review of commercially available oral formulations", Journal of Pharmaceutical Sciences, vol. 97, No. 5 (May 1, 2008) XP055121290.
Eloisa Comiran et al "Lisdexamfetamine: A pharmacokinetic review", European Journal of Pharmaceutical Sciences, vol. 89, pp. 172-179 (Apr. 26, 2016) XP029555330.
International Search Report and Written Opinion of the International Searching Authority, issued in PCT/EP2020/06077, dated May 19, 2020; ISA/EP.

* cited by examiner

*Primary Examiner* — Daniel R Carcanague
*Assistant Examiner* — Gillian A Hutter
(74) *Attorney, Agent, or Firm* — Harness, Dickey & Pierce, P.L.C.

(57) ABSTRACT

Oral pharmaceutical solution comprising a pharmaceutically acceptable salt of lisdexamfetamine, and a pharmaceutically acceptable aqueous carrier comprising a buffer and a cosolvent selected from the group consisting of a glycol, a polyol, and a mixture thereof, wherein the pH of the solution is from 5.5 to 9.0. The oral pharmaceutical solution presents excellent physicochemical stability, even under alkaline conditions.

15 Claims, No Drawings

ORAL SOLUTIONS COMPRISING LISDEXAMFETAMINE SALTS

CROSS-REFERENCE TO RELATED APPLICATIONS

This application is a 371 U.S. National Phase of International Application No. PCT/EP2020/060777, filed Apr. 16, 2020, which claims priority to European Patent Application No. 19386059.0, filed Dec. 30, 2019. The entire disclosures of the above applications are incorporated herein by reference.

FIELD OF THE INVENTION

The present invention relates to oral pharmaceutical solutions comprising a pharmaceutically acceptable salt of lisdexamfetamine.

BACKGROUND OF THE INVENTION

Lisdexamfetamine or L-lysine-d-amfetamine (LDX; formerly NRP-104), (2S)-2,6-diamino-N-[(1S)-1-methyl-2-phenylethyl] hexanamide dimethanesulfonate) was first disclosed in U.S. Pat. No. 7,105,486.

Lisdexamfetamine has the following structure.

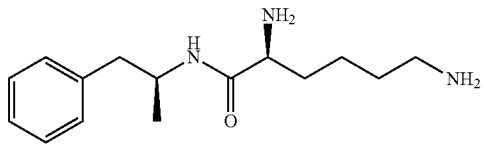 [SMILES: C[C@@H](Cc1ccccc1)NC(=O)[C@@H](N)CCCCN]

Lisdexamfetamine, sold under the brand names Elvanse® (DK, GB, SE), Tyvense® (IE), Venvanse® (BR), Vyvanse® (US, CA) among others, is a medication that is used to treat attention deficit hyperactivity disorder (ADHD) in people over the age of six as well as for moderate to severe binge eating disorder in adults.

Lisdexamfetamine is a pro-drug of dexamfetamine and contains D-amfetamine covalently linked to the essential amino acid L-lysine. It lacks stimulant properties but is hydrolyzed in the gut wall to release d-amfetamine. As it is an inactive material, it cannot be taken nasally, intravenously or in any other way b achieve an illicit stimulant effect. Furthermore, the metabolic hydrolysis of the pro-drug takes some time and as such the formulation has an element of in-built controlled release notwithstanding that the product may contain only excipients employed in immediate release dosage forms. The product can deliver dexamfetamine over a period of about 8 hours and so it is useful to treat ADHD in paediatric populations (aged 6 to 12), but the extent of its duration is not considered to be sufficient to treat adolescent and adult populations having much longer active days.

Lisdexamfetamine is currently commercially available only as 10, 20, 30, 40, 50, 60 and 70 hard capsules or chewable tablets. Each capsule or chewable tablet contains 10, 20, 30, 40, 50, 60 or 70 mg lisdexamfetamine dimesylate, equivalent to 5.8 mg, 11.6 mg, 17.3 mg, 23.1 mg, 28.9 mg or 34.7 mg lisdexamfetamine, respectively.

Lisdexamfetamine dimesylate has the following structure.

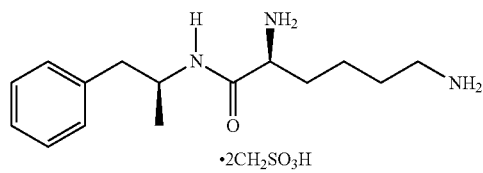 [SMILES: C[C@@H](Cc1ccccc1)NC(=O)[C@@H](N)CCCCN]

Although oral solid dosage forms such as capsules are very popular for reasons that are mainly due to ease of management, for certain users (e.g. children) these forms are not necessarily a convenient option, especially due to difficulty in swallowing these forms. This lack of convenience results in high incidence of non-compliance and ineffective therapy.

Moreover, the Patient Information Leaflet (PIL) of Vyvanse®& Elvanse® discloses a dosing scheme for children over 6 years of age according to which the dosage should be individualised according to the therapeutic needs and response of the patient, while careful dose titration is necessary at the start of treatment with Vyvanse® or Elvanse®. The concept of tailored treatment sets as prerequisite pharmaceutical forms, such as oral solutions, that enable dose fractioning.

According to WO 2006/121552, lisdexamfetamine can be alternatively formulated as an aqueous solution, or a sterile composition. Compositions in these cases may be stored in freeze-dried form and may be associated with a stabilizing agent such as a carbohydrate. In use, the composition may be deployed in an aqueous solution containing salts, e.g., NaCl, detergents such as sodium dodecyl sulfate (SDS), and other components. Furthermore, according to this patent document lisdexamfetamine may be formulated as liquid dispersion for oral administration, for example as a syrup, emulsion, or suspension. However, no specific liquid based compositions are described in WO 2006/121552.

There are a number of challenges surrounding the development of liquid based formulations such as stability and solubility not adequately elaborated in the prior art. In fact, active pharmaceutical agents in liquid forms are more susceptible to chemical and physical instability than in the solid state. In addition to the solubility, the active pharmaceutical agent needs to be physically and chemically stable in the oral solution. Trace amounts of impurities from active pharmaceutical agents or excipients and the pH of the solution may cause the degradation of the active pharmaceutical agent and this may cause an increase in instability when the solution is consistently introduced into the atmosphere.

Although lisdexamfetamine acid addition salts, such as lisdexamfetamine dimesylate and lisdexamfetamine hydrochloride are very soluble in water, the desire for the development of an oral solution of a lisdexamfetamine salt is complicated by the fact that the molecule degrades significantly at basic (alkaline) and oxidative conditions.

According to Carlos G. et. al., "*Assessment of lisdexamfetamine dimesylate stability and identification of its degradation product by NMR spectroscopy*" Drug Dev Ind Pharm. 2019 January, although lisdexamfetamine dimesylate degrades at both acidic and alkaline conditions, it is more hydrolysis-susceptible under alkaline conditions.

According to Shenghua G. et. al., "*Identification, characterization and quantification of process-related and degradation impurities in lisdexamfetamine dimesylate: identification of two new compounds*", molecules. 2018

December; 23(12): 3125, lisdexamfetamine can produce at least Imp-A, Imp-B or Imp-C in alkaline conditions, whereas at least Imp-M is produced under oxidative conditions.

The main known degradation impurities of lisdexamfetamine are shown below.

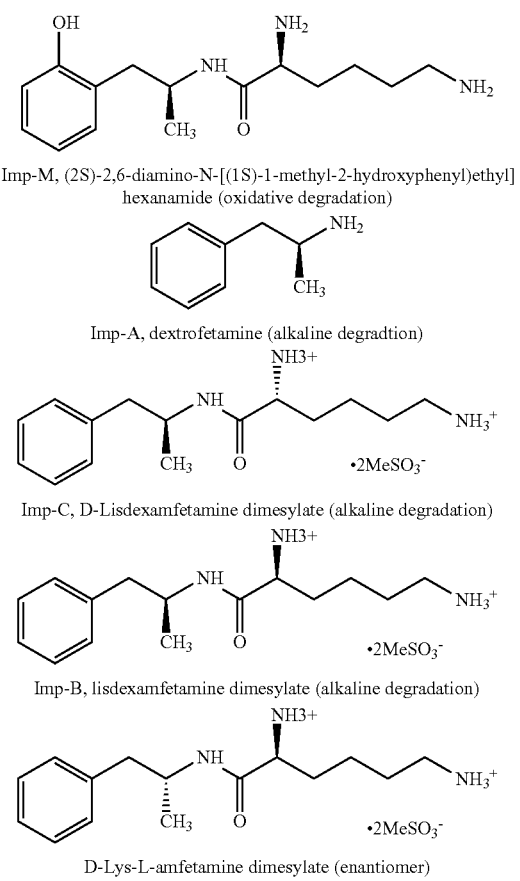

Imp-M, (2S)-2,6-diamino-N-[(1S)-1-methyl-2-hydroxyphenyl)ethyl] hexanamide (oxidative degradation)

Imp-A, dextrofetamine (alkaline degradtion)

Imp-C, D-Lisdexamfetamine dimesylate (alkaline degradation)

Imp-B, lisdexamfetamine dimesylate (alkaline degradation)

D-Lys-L-amfetamine dimesylate (enantiomer)

Technically, the biggest challenge is the development of liquid based formulations. using stabilizing excipients with low toxicity in the lowest feasible concentrations without compromising the stability of the formulations. In other words, the low concentrations of stabilizing excipients may contribute to reducing the potential for toxicological effects, but they may be insufficient for achieving the required level of physicochemical stability.

The present invention overcomes the problems of the prior art and provides an oral pharmaceutical solution, comprising a pharmaceutically acceptable salt of lisdexamfetamine, which exhibits excellent stability and extended lifetime.

SUMMARY OF INVENTION

The present invention provides a physicochemically stable oral pharmaceutical solution comprising a pharmaceutically acceptable salt of lisdexamfetamine.

The oral pharmaceutical solution according to the invention comprises a pharmaceutically acceptable salt of lisdexamfetamine, and a pharmaceutically acceptable aqueous carrier comprising a buffer and a cosolvent selected from the group consisting of a glycol, a polyol, and a mixture thereof, wherein the pH of the solution is from 5.5 to 9.0.

The oral pharmaceutical solution according to the invention presents excellent physicochemical stability.

The present invention has the advantage that it provides a stable oral pharmaceutical solution of a pharmaceutically acceptable salt of lisdexamfetamine, by inhibiting hydrolysis and oxidation that typically occur after extended storage.

Further to that, oral solutions of the present invention provide the best alternative over conventional capsule or chewable tablet dosage forms. Apart from achieving better patient compliance, oral solutions of the present invention offer unique advantages such as more reproducible bioavailability and an option of a flexible dosing regimen based on body weight or body surface area.

DETAILED DESCRIPTION OF THE INVENTION

The present invention provides a stable oral pharmaceutical solution comprising a pharmaceutically acceptable salt of lisdexamfetamine in association with a pharmaceutically acceptable liquid carrier.

The term "stable" as used herein, refers to both physical and chemical stability, wherein not more than 1.0% of total degradation impurities are formed on storage at 40° C. and 75% relative humidity over a period of four weeks.

According to David W. Goodman, "Lisdexamfetamine dimesylate. The first prodrug stimulant" Psychiatry (Edgmont). 2007 August; 4(8): 39-45, the pH solubility profile of lisdexamfetamine dimesylate in saturated buffered aqueous solutions (pH 1-13) was determined by a high-pressure liquid chromatography assay that was specific for lisdexamfetamine dimesylate. Lisdexamfetamine dimesylate was proved to be highly soluble within a physiologically relevant pH range (pH 1-8). Its solubility profile was not affected by the pH of the solution, and increasing the pH from 8 to 13 resulted only in modest reductions in lisdexamfetamine dimesylate solubility.

Although lisdexamfetamine acid addition salts, such as lisdexamfetamine dimesylate are very soluble in water, the desire for the development of an oral solution of a lisdexamfetamine salt is complicated by the fact that the molecule degrades significantly at alkaline and oxidative conditions.

Unexpectedly, it has been found that the inclusion of common antioxidants such as sodium metabisulfite and butylated hydroxyanisole to oral solutions comprising a pharmaceutically acceptable salt of lisdexamfetamine did not actually prevent decomposition of the active agent after storage.

Further to that, inclusion of certain additives commonly used as stabilizers in aqueous oral solutions, such as α-cyclodextrins, β-cyclodextrins and γ-cyclodextrins did not actually enhance the stability of lisdexamfetamine salts. The same applies to the inclusion of commonly used surfactants/stabilizers, such as sorbitan oleate ester and polyoxyethylene sorbitan monooleate, which also did not enhance the stability of lisdexamfetamine salts.

On the other hand, it has now been found that, although pharmaceutically acceptable salts of lisdexamfetamine are highly soluble in the pH range of 1 to 13, which means that there is no need of addition of a cosolvent, their physicochemical stability in aqueous solutions is surprisingly enhanced by the addition of certain non-aqueous cosolvents such as a glycol, or a polyol or a mixture thereof. Furthermore, it has been found that the addition of such a cosolvent leads to a stable and homogenous solution of a pharmaceutically acceptable salt of lisdexamfetamine, not only around neutral pH, but also in alkaline pH. This finding is unexpected since it does not apply to other cosolvents, commonly used in oral solutions. For example, the addition of diethylene glycol monoethyl ether, or macrogol (15)-hydroxystearate does not enhance the stability of lisdexamfetamine salts in an aqueous solution.

The oral pharmaceutical solution according to the invention comprises a pharmaceutically acceptable salt of lisdexamfetamine and a pharmaceutically acceptable aqueous carrier comprising a buffer and a cosolvent selected from the group consisting of a glycol, a polyol, and a mixture thereof, wherein the pH of the solution is from 5.5 to 9.0.

As used throughout this description and claims, a "glycol" may be propylene glycol, polyethylene glycol or any other pharmaceutically acceptable polyalkylene glycol product such as those known in the art as the "PEG" series, or mixtures thereof. Preferably, the glycol is selected from the group consisting of propylene glycol and low molecular weight polyethylene glycols i.e. liquid polyethylene glycols with average molecular weight lower than 600. More preferably, the glycol is polyethylene glycol with average molecular weight lower than 600. This glycol provides the additional advantage of masking the bitter taste of pharmaceutically acceptable salts of lisdexamfetamine.

As used throughout this description and claims, the term "polyol" (polyhydric alcohol) refers to pharmaceutical excipients containing multiple hydroxyl groups. Although the term "polyol" includes sugar alcohols, it does not include sugars, i.e. carbohydrates, such as sucrose, glucose, dextrose, fructose and galactose. Polyols are generally used as sweeteners and bulking agents. They occur naturally in foods and come from plant products such as fruits and berries. Typical examples of suitable polyols according to the invention are sugar alcohols such as, maltitol, glycerol, sorbitol, xylitol, erythritol, isomalt and lactitol, as well as polyvinyl alcohol. Some of these polyols, such as the sugar alcohols, impart a sweet taste to the overall solution and act as a preservative. Preferably, the polyol is selected from the group consisting of maltitol, glycerol, mannitol, sorbitol and xylitol. More preferably, the polyol is maltitol. Maltitol substantially masks the bitter taste of pharmaceutically acceptable salts of lisdexamfetamine as a result of its sweet taste and in addition, it is non-cariogenic. Maltitol is used as a low-calorie sweetening agent, it is slowly absorbed and exhibits a low effect on blood glucose, which makes it more suitable for people. It is not metabolized by oral bacteria, so it does not promote tooth decay. It has an additional advantage in that crystallization is less likely to occur.

Any pharmaceutically acceptable system which acts as a buffer in the pH region of the invention can be used in the oral pharmaceutical solution. Buffering agents may include but not limited to ascorbic acid, acetic acid, tartaric acid, citric acid monohydrate, sodium citrate, potassium citrate, acetic acid, sodium acetate, sodium hydrogen phosphate, sodium dihydrogen phosphate, calcium hydrogen phosphate, calcium dihydrogen phosphate or mixtures thereof.

The oral pharmaceutical solution according to the invention may comprise any pharmaceutically acceptable salt of lisdexamfetamine such as 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like. Preferably, the oral pharmaceutical solution according to the invention comprises lisdexamfetamine dimesylate or lisdexamfetamine hydrochloride. More preferably, the oral pharmaceutical solution according to the invention comprises lisdexamfetamine dimesylate.

Preferably, the oral pharmaceutical solution according to the invention comprises from 1 mg/ml to 40 mg/ml of a pharmaceutically acceptable salt of lisdexamfetamine. More preferably, the solution comprises from 5 mg/ml to 30 mg/ml of a pharmaceutically acceptable salt of lisdexamfetamine. Even more preferably, the solution comprises from 10 mg/ml to 20 mg/ml of a pharmaceutically acceptable salt of lisdexamfetamine.

Preferably, the oral pharmaceutical solution according to the invention comprises from 5 mg/ml to 30 mg/ml of lisdexamfetamine dimesylate.

More preferably, the oral pharmaceutical solution according to the invention comprises from 10 mg/ml to 20 mg/ml of lisdexamfetamine dimesylate.

Preferably, the total concentration of the cosolvent in the oral pharmaceutical solution according to the invention is from 5 to 300 mg/ml. More preferably, the total concentration of the cosolvent is from 50 mg/ml to 250 mg/ml. Even more preferably, the total concentration of the cosolvent is from 100 mg/ml to 200 mg/ml.

Preferably, the pH of the solution is from 6.0 to 8.5.

More preferably, the pH of the solution is from 6.5 to 8.0.

According to a preferred embodiment, the oral pharmaceutical solution according to the invention comprises from 1 mg/ml to 40 mg/ml of a pharmaceutically acceptable salt of lisdexamfetamine, and a pharmaceutically acceptable aqueous carrier comprising a buffer, and a cosolvent selected from the group consisting of a glycol a polyol, and a mixture thereof, wherein the total concentration of the cosolvent is from 5 mg/ml to 300 mg/ml, wherein the pH of the solution is from 5.5 to 9.0.

According to a more preferred embodiment, the oral pharmaceutical solution according to the invention comprises from 1 mg/ml to 40 mg/ml of a pharmaceutically acceptable salt of lisdexamfetamine, and a pharmaceutically acceptable aqueous carrier comprising a buffer and a cosolvent selected from the group consisting of maltitol, glycerol, mannitol, sorbitol, xylitol, propylene glycol, low molecular weight polyethylene glycols, and a mixture thereof, wherein the total concentration of the cosolvent is from 5 mg/ml to 300 mg/ml, wherein the pH of the solution is from 5.5 to 9.0.

Preferably, the oral pharmaceutical solution according to the invention is free of any antioxidant, such as sodium metabisulfite, butylated hydroxyanisole, butylated hydroxytoluene, ethylenediamine tetraacetic acid, ascorbic acid, α-tocopherol, and propyl gallate.

The oral pharmaceutical solution according to the invention may also optionally contain additional excipients commonly used in preparing oral liquid compositions, such as antimicrobial preservatives, viscosity adjusting agents, sweeteners and flavouring agents.

Antimicrobial preservatives may include but not limited to sodium benzoate, benzoic acid, boric acid, sorbic acid and their salts thereof, benzyl alcohol, parahydroxy benzoic acids and their alkyl esters, methyl, ethyl and propyl parahydroxy benzoates and their salts or mixtures thereof.

Sweeteners may include but not limited to sucralose, aspartame, acesulfame-K, thaumatin, mogroside, saccharin and salts thereof, sodium cyclamate, glucose, sucrose, lactose, fructose, erythritol, glycyrrhizin, monosodium glycyrrhizinate, monoammonium glycyrrhizinate, dextrose or mixtures thereof.

Flavouring agents used in the oral pharmaceutical solution according to the invention may include but not limited to fruit flavours such as orange, banana, strawberry, cherry, wild cherry, lemon and the like and other flavourings, such as cardamom, anise, mint, menthol, vanillin, bubble gum or mixtures thereof.

The oral pharmaceutical solution according to the invention is preferably supplied as a multidose preparation. Each dose from a multidose container, such as amber type III glass 50 or 100 ml bottles sealed with child resistant, tamper evident screw caps, can be administered by means of a device suitable for measuring the prescribed volume. The device is usually a spoon or a cup for volumes of 5 ml or multiples thereof, or an oral syringe for other volumes.

The oral pharmaceutical solution of the present invention may be prepared using methods well known in the art and using regular manufacturing equipment.

For example, it may be prepared using the following process:

The active substance and the excipients are weighed. Purified water is added into a vessel. The pharmaceutically acceptable salt of lisdexamfetamine and the cosolvent, are successively dissolved into purified water under stirring. A pH buffer solution, prepared in a different vessel, is added under continuous stirring until the pharmaceutically acceptable salt of lisdexamfetamine is completely dissolved. Preservative, if present, is also added under continuous stirring until complete dissolution. Flavour and the remaining excipients, if present, are successively added under continuous stirring, until complete dissolution. The pH of the solution is adjusted with a quantity of the buffer solution to the desired value. Finally, the volume is adjusted with purified water.

The final solution is optionally filtered over a 10 μm filter, and filled preferably in light-protective containers, such as amber type III glass 50 or 100 ml bottles sealed with child resistant, tamper evident screw caps.

EXAMPLES

Example 1

The purpose of this experiment was to evaluate the influence of common antioxidants on the stability of lisdexamfetamine dimesylate solutions.

These lisdexamfetamine dimesylate compositions were prepared in the following manner:

In the main vessel, 80% of the amount of purified water was transferred under magnetic stirring. The amounts of citric acid and sodium citrate were slowly added until complete dissolution. The amount of lisdexamfetamine dimesylate was slowly added in the main vessel under stirring until complete dissolution. The pH value of the solution was measured and adjusted, if needed, at the optimum value. Purified water was added to the final batch size.

Storage conditions of temperature (4000) and relative humidity (75%) applied for a period of four weeks. Quantification of lisdexamfetamine dimesylate and its impurities, in the compositions prepared, was performed by HPLC.

TABLE 1

| | | Compositions | | |
| --- | --- | --- | --- | --- |
| | | Trial 1 | Trial 2 | Trial 3 |
| Function | Component | | mg/ml | |
| API | Lisdexamfetamine dimesylate | 10 | 10 | 10 |
| Antioxidant | Sodium metabisulfite | — | 1 | — |
| | BHA | — | — | 0.5 |
| buffering agent | Citric acid monohydrate | 2.0 | 2.0 | 2.0 |
| | Sodium Citrate dihydrate | 0.9 | 0.9 | 0.9 |
| pH adjustment agent | Citric acid (10% w/v)/ Sodium citrate (10% w/v) | Qs to pH 6.5 | Qs to pH 6.5 | Qs to pH 6.5 |
| Diluent | PW | | Qs to 1 mL | |

TABLE 2

Stability results

| | Parameter | Trial 1 | Trial 2 | Trial 3 |
|---|---|---|---|---|
| T = 0 | pH | 6.46 | 6.40 | 6.45 |
| | Assay | n/a | 97.3% | 98.6% |
| | Impurities | Not Detected | RRT 0.46: 0.02%<br>RRT 0.66: 0.01%<br>RRT 0.94: 005%<br>RRT 0.96: 0.03% | Not Detected |
| | Total impurities | Not Detected | 0.11% | Not Detected |
| 40° C./75% 4 weeks | pH | 6.46 | 6.30 | 6.40 |
| | Assay | n/a | 95.0% | 95.8% |
| | Impurities | Dxtroamfet: 0.02%<br>D-Ldxamfet: 0.04%<br>RRT 0.44: 0.04%<br>RRT 0.45: 0.08%<br>RRT 0.47: 0.07%<br>RRT 0.69: 0.04%<br>RRT 0.70: 0.07%<br>RRT 0.72: 0.13%<br>RRT 0.83: 0.01%<br>RRT 0.94: 0.22%<br>RRT 0.97: 0.19%<br>RRT 1.08: 0.04%<br>RRT 1.09: 0.01%<br>RRT 1.14: 0.05% | Dxtroamfet: 0.02%<br>D-Ldxamfet: 0.05%<br>RRT 0.44: 0.04%<br>RRT 0.45: 0.10%<br>RRT 0.47: 0.07%<br>RRT 0.49: 0.02%<br>RRT 0.64: 0.01%<br>RRT 0.69: 0.04%<br>RRT 0.70: 0.07%<br>RRT 0.72: 0.12%<br>RRT 0.73: 0.01%<br>RRT 0.75: 0.01%<br>RRT 0.83: 0.01%<br>RRT 0.94: 0.33%<br>RRT 0.97: 0.18%<br>RRT 1.08: 0.04%<br>RRT 1.09: 0.01%<br>RRT 1.14: 0.05% | Dxtroamfet: 0.02%<br>D-Ldxamfet: 0.05%<br>RRT 0.44: 0.04%<br>RRT 0.45: 0.11%<br>RRT 0.47: 0.06%<br>RRT 0.49: 0.02%<br>RRT 0.64: 0.01%<br>RRT 0.69: 0.05%<br>RRT 0.70: 0.06%<br>RRT 0.72: 0.11%<br>RRT 0.73: 0.02%<br>RRT 0.94: 0.33%<br>RRT 0.97: 0.18%<br>RRT 1.08: 0.04%<br>RRT 1.09: 0.01%<br>RRT 1.14: 0.02% |
| | Total impurities | 1.01% | 1.18% | 1.13% |

Dxtroamfet: Dextroamfetamine
D-Ldxamfet: D-Lisdexamfetamine

Surprisingly it was found that the addition of antioxidants did not prevent decomposition of the active agent after storage. Instead, the decomposition was very significant. Furthermore, inclusion of 200 mg/ml of diethylene glycol monomethyl ether to the compositions of Table 1 did not enhance the stability of the active agent.

Example 2

The purpose of this experiment was to evaluate the influence of pH between 2.5 and 5.5 on the stability of lisdexamfetamine dimesylate solutions, when maltitol is used as cosolvent.

These compositions were prepared in the following manner:

In the main vessel, 80% of the amount of purified water was transferred under magnetic stirring. The amounts of citric acid and sodium citrate were slowly added under stirring until complete dissolution. In the main vessel, the amount of lisdexamfetamine dimesylate and maltitol was slowly added under stirring until complete dissolution. The pH value of the solution was measured and adjusted, if needed, at the optimum value. Purified water was added to the final batch size.

Storage conditions of temperature (40° C.) and relative humidity (75%) applied for a period of four weeks. Quantification of lisdexamfetamine dimesylate and its impurities, in the compositions prepared, was performed by HPLC.

TABLE 2a

Compositions

| Function | Component | Trial 1' (pH ~2.5) | Trial 2' (pH ~3.5) | Trial 3' (pH ~4.5) | Trial 4' (pH ~5.5) |
|---|---|---|---|---|---|
| | | mg/ml | | | |
| Cosolvent | Maltitol | 100 | 100 | 100 | 100 |
| API | Lisdexamfetamine dimesylate | 10 | 10 | 10 | 10 |
| Buffering agent | Citric acid monohydrate | 3.0 | 2.0 | 1.0 | 0.8 |
| | Sodium Citrate dihydrate | 0.1 | 0.9 | 1.2 | 3.0 |
| pH adjustment agent | Citric acid (10% w/v)/<br>Sodium citrate (10% w/v) | Qs to pH 2.5 | Qs to pH 3.5 | Qs to pH 4.5 | Qs to pH 5.5 |
| Diluent | PW | Qs to 1 mL | | | |

TABLE 2b

Stability study results

| | Parameter | Trial 1' (pH ~2.5) | Trial 2' (pH: ~3.5) | Trial 3' (pH: ~4.5) | Trial 4' (pH ~5.5) |
|---|---|---|---|---|---|
| T = 0 | pH | 2.8 | 3.7 | 4.7 | 5.7 |
| | Assay | 101.1% | 97.0% | 96.7% | 103.8% |
| | Impurities | Not Detected | Not Detected | Not Detected | Not Detected |
| | Total impurities | Not Detected | Not Detected | Not Detected | Not Detected |
| 40° C./75% 2 weeks | pH | 2.8 | 3.7 | 4.7 | 5.7 |
| | Assay | NA | NA | NA | NA |
| | Dxtroamfet: | 0.14% | 0.39% | 0.28% | 0.03% |
| | RRT 0.68: | 0.18% | 0.68% | 0.84% | 0.26% |
| | RRT 0.72: | 0.35% | 1.2% | 1.4% | 0.41% |
| | RRT 0.75: | Not detected | 0.06% | 0.09% | 0.05% |
| | Total impurities | 0.67% | 2.3% | 2.6% | 0.75% |
| 40° C./75% 4 weeks | pH | 2.8 | 3.7 | 4.7 | 5.7 |
| | Assay | 100.4% | 95.7% | 94.3% | 102.1% |
| | Dxtroamfet: | 0.34% | 0.93% | 0.73% | 0.06% |
| | RRT 0.68: | 0.36% | 1.2% | 1.5% | 0.57% |
| | RRT 0.72: | 0.46% | 1.6% | 2.4% | 0.79% |
| | RRT 0.75 | Not detected | 0.07% | 0.11% | 0.06% |
| | Total impurities | 1.2% | 3.8% | 4.7% | 1.5% |

Dxtroamfet: Dextroamfetamine

From this study, it is concluded that even in the presence of maltitol as cosolvent, control of pH is critical for the stability of lisdexamfetamine dimesylate and that pH values up to 5.5 do not provide the desired stability of lisdexamfetamine dimesylate.

Example 3

The purpose of this experiment was also to evaluate the influence of pH between 6 and 8.5 on the stability of lisdexamfetamine dimesylate solutions, when maltitol is used as cosolvent.

These lisdexamfetamine dimesylate solutions were prepared as described in example 2.

Storage conditions of temperature (40° C.) and relative humidity (75%) applied for a period of four weeks. Quantification of lisdexamfetamine dimesylate and its impurities, in the compositions prepared, was performed by HPLC.

TABLE 3a

Compositions

| Function | Component | Trial 5' (pH ~6.0) | Trial 6' (pH ~6.5) mg/ml | Trial 7' (pH ~6.5) |
|---|---|---|---|---|
| API | Lisdexamfetamine dimesylate | 10 | 10 | 10 |
| Cosolvent | Maltitol | 100 | 100 | 100 |
| pH adjustment agent | Citric acid (10% w/v))/Sodium citrate (10% w/v) | Qs to pH 6.0 | Qs to pH 6.5 | — |
| | Disodium hydrogen phosphate(10% w/v)/Sodium dihydrogen phosphate (10% w/v) | — | — | Qs to pH 6.5 |
| Diluent | Purified water | | Qs to 1 mL | |

TABLE 3b

Compositions

| Function | Component | Trial 8' (pH ~7.0) | Trial 9' (pH ~7.5) | Trial 10' (pH ~8.5) |
|---|---|---|---|---|
| API | Lisdexamfetamine dimesylate | 10 | 10 | 10 |
| Cosolvent | Maltitol | 100 | 100 | 100 |
| pH adjustment agent | Disodium hydrogen phosphate(10% w/v)/Sodium dihydrogen phosphate (10% w/v) | Qs to pH 7.0 | Qs to pH 7.5 | Qs to pH 8.5 |
| Diluent | Purified water | | Qs to 1 mL | |

TABLE 3c

Stability results

| | Parameter | Trial 5' (pH ~6.0) | Trial 6' (pH ~6.5) | Trial 7' (pH ~6.5) |
|---|---|---|---|---|
| T = 0 | pH | 5.98 | 6.46 | 6.46 |
| | Assay | 102.3% | 104.3% | 97.4% |
| | Impurities | Not Detected | Not Detected | Not Detected |
| | Total impurities | Not Detected | Not Detected | Not Detected |
| 40° C./75% 4 weeks | pH | 5.94 | 6.45 | 6.46 |
| | Assay | 101.2% | 104.8% | 97.9% |
| | Impurities | D-Ldxamfet: 0.03% | | D-Ldxamfet: 0.06% |
| | | RRT 0.70: 0.13% | RRT 0.70: 0.03% | |
| | | RRT 0.72: 0.21% | RRT 0.72: 0.05% | |
| | | RRT 0.75: 0.02% | | |
| | Total impurities | 0.39% | 0.08% | 0.06% |

TABLE 3d

Stability results

| | Parameter | Trial 8' (pH ~7.0) | Trial 9' (pH ~7.5) | Trial 10' (pH ~8.5) |
|---|---|---|---|---|
| T = 0 | pH | 6.95 | 7.46 | 8.56 |
| | Assay | 100.8% | 99.6% | 99.3% |
| | Impurities | ND | RRT 0.46: 0.01% | RRT 0.46: 0.02% |
| | Total impurities | ND | 0.01% | 0.02% |
| 40° C./75% 4 weeks | pH | 6.94 | 7.46 | 8.48 |
| | Assay | 101.3% | 100.5% | 99.0% |
| | Impurities | D-Ldxamfet: 0.11% | | Dxtroamfet: 0.01% |
| | | | Dxtroamfet: 0.01% | D-Ldxamfet: 0.18% |
| | | | D-Ldxamfet: 0.16% | RRT 0.72: 0.01% |
| | | | | RRT 0.75: 0.02% |
| | Total impurities | 0.11% | 0.17% | 0.22% |

From this study, it is surprisingly concluded that in the presence of maltitol as cosolvent the stability of lisdexamfetamine dimesylate is significantly increased when the pH of the solution is at least 6. Moreover, excellent stability of lisdexamfetamine dimesylate is achieved even under alkaline conditions.

Example 4

Preferred liquid compositions of lisdexamfetamine dimesylate.

These lisdexamfetamine dimesylate compositions were prepared in the following manner:

Purified water was added into a vessel. Lisdexamfetamine dimesylate and the cosolvent(s), are successively dissolved into purified water under stirring. A pH buffer solution, prepared in a different vessel, was added under continuous stirring until lisdexamfetamine dimesylate was completely dissolved. Preservative, was also added under continuous stirring until complete dissolution. The flavour was then added under continuous stirring, until complete dissolution. The pH of the solution was adjusted with a quantity of the buffer solution to the desired value. Finally, the volume was adjusted with purified water.

Storage conditions of temperature (40° C.) and relative humidity (75%) applied for a period of four weeks. Quantification of lisdexamfetamine dimesylate and its impurities, in the compositions prepared, was performed by HPLC.

TABLE 4a preferred compositions according to the present invention

| | Composition I | Composition II mg/ml | Composition III |
|---|---|---|---|
| Active ingredient | | | |
| Lisdexamfetamine dimesylate | 10 | 10 | 10 |
| Excipients | | | |
| Maltitol | 50 | — | — |
| Propylene glycol | — | 200 | — |
| PEG-400 | — | — | 100 |
| Sodium benzoate | 0.1 | 0.1 | 0.1 |

TABLE 4a-continued preferred compositions according to the present invention

| | Composition I | Composition II | Composition III |
|---|---|---|---|
| | | mg/ml | |
| Flavour mint | 0.5 | 0.5 | 0.5 |
| Purified water | q.s. 1 ml | q.s. 1 ml | q.s. 1 ml |
| Phosphate buffer solution | pH: 6.5 | pH: 6.5 | pH: 6.5 |

TABLE 4b preferred compositions according to the present invention

| | Composition IV | Composition V | Composition VI |
|---|---|---|---|
| | | mg/ml | |
| Active ingredient | | | |
| Lisdexamfetamine dimesylate | 10 | 10 | 10 |
| Excipients | | | |
| Glycerol | 100 | — | — |
| Sorbitol | — | 100 | — |
| Xylitol | — | 100 | 150 |
| Sodium benzoate | 0.1 | 0.1 | 0.1 |
| Flavour mint | 0.5 | 0.5 | 0.5 |
| Purified water | q.s. 1 ml | q.s. 1 ml | q.s. 1 ml |
| Phosphate buffer solution | pH: 6.5 | pH: 6.5 | pH: 6.5 |

TABLE 4c

| | | Stability results | | |
|---|---|---|---|---|
| | Parameter | Composition I | Composition II | Composition III |
| T = 0 | pH | 6.48 | 6.46 | 6.46 |
| | Assay | 102.3% | 101.3% | 99.9% |
| | Impurities | ND | ND | ND |
| | Total impurities | ND | ND | ND |
| | pH | 6.46 | 6.45 | 6.46 |
| | Assay | 101.2% | 100.8% | 99.6% |
| 40° C./75% 4 weeks | Impurities | D-Ldxamfet: 0.03% | | D-Ldxamfet: 0.06% |
| | | RRT 0.70: 0.13% | RRT 0.70: 0.03% | |
| | | RRT 0.72: 0.11% | RRT 0.72: 0.05% | |
| | | RRT 0.75: 0.02% | | |
| | Total impurities | 0.29% | 0.08% | 0.06% |

TABLE 4d

| | Parameter | Composition IV | Composition V | Composition VI |
|---|---|---|---|---|
| Stability results | | | | |
| T = 0 | pH | 6.48 | 6.46 | 6.46 |
| | Assay | 100.3% | 100.9% | 99.8% |
| | Impurities | ND | ND | ND |
| | Total impurities | ND | ND | ND |
| 40° C./75% 4 weeks | pH | 6.46 | 6.45 | 6.46 |
| | Assay | 99.2% | 100.3% | 99.6% |
| | Impurities | D-Ldxamfet: 0.03% | D-Ldxamfet: 0.03% | Dxtroamfet: 0.02% |
| | | RRT 0.72: 0.09% | RRT 0.72: 0.08% | D-Ldxamfet: 0.06% |
| | | RRT 0.75: 0.12% | RRT 0.75: 0.04% | RRT 0.72: 0.09% |
| | | | | RRT 0.75: 0.06% |
| | | | | RRT 0.79: 0.05% |
| | Total impurities | 0.24% | 0.15% | 0.28% |

Dxtroamfet: Dextroamfetamine
D-Ldxamfet: D-Lisdexamfetamine

The invention claimed is:

1. Oral pharmaceutical solution comprising from 1 mg/ml to 40 mg/ml of a pharmaceutically acceptable salt of lisdexamfetamine and a pharmaceutically acceptable aqueous carrier comprising a buffer and a cosolvent selected from the group consisting of a glycol, a polyol and a mixture thereof, wherein the pH of the solution is from 5.5 to 9.0.

2. Oral pharmaceutical solution according to claim 1, wherein the solution is free of any antioxidant.

3. Oral pharmaceutical solution according to claim 1, wherein the solution is free of an antioxidant selected from the group consisting of sodium metabisulfite, butylated hydroxy anisole, butylated hydroxytoluene, ethylenediamine tetraacetic acid, ascorbic acid, α-tocopherol, and propyl gallate.

4. Oral pharmaceutical solution according to claim 1, wherein the cosolvent is selected from the group consisting of maltitol, glycerol, mannitol, sorbitol, xylitol, propylene glycol, low molecular weight polyethylene glycol and a mixture thereof.

5. Oral pharmaceutical solution according to claim 1, wherein the cosolvent is selected from the group consisting of maltitol and low molecular weight polyethylene glycol.

6. Oral pharmaceutical solution according to claim 1, wherein the cosolvent is maltitol.

7. Oral pharmaceutical solution according to claim 1, wherein the total concentration of the cosolvent is from 5 mg/ml to 300 mg/ml.

8. Oral pharmaceutical solution according to claim 1, wherein the total concentration of the cosolvent is from 50 mg/ml to 250 mg/ml.

9. Oral pharmaceutical solution according to claim 1, wherein the total concentration of the cosolvent is from 100 mg/ml to 200 mg/ml.

10. Oral pharmaceutical solution according to claim 1, wherein the pH of the solution is from 6.0 to 8.5.

11. Oral pharmaceutical solution according to claim 1, wherein the pH of the solution is from 6.5 to 8.0.

12. Oral pharmaceutical solution according to claim 1, wherein the concentration of the pharmaceutically acceptable salt of lisdexamfetamine is from 5 mg/ml to 30 mg/ml.

13. Oral pharmaceutical solution according to claim 1, wherein the concentration of the pharmaceutically acceptable salt of lisdexamfetamine is from 10 mg/ml to 20 mg/ml.

14. Oral pharmaceutical solution according to claim 1, wherein the pharmaceutically acceptable salt of lisdexamfetamine is selected from the group consisting of lisdexamfetamine dimesylate and lisdexamfetamine hydrochloride.

15. Oral pharmaceutical solution according to claim 1, wherein the pharmaceutically acceptable salt of lisdexamfetamine is lisdexamfetamine dimesylate.

\* \* \* \* \*